(12) United States Patent
Martin et al.

(10) Patent No.: US 9,242,042 B2
(45) Date of Patent: Jan. 26, 2016

(54) DRUG DELIVERY SYSTEM INCLUDING A DRUG-CONTAINER HOLDER AND A PUMP ASSEMBLY

(75) Inventors: James F. Martin, Lebanon, OH (US); Paul J. Niklewski, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 752 days.

(21) Appl. No.: 12/506,385

(22) Filed: Jul. 21, 2009

(65) Prior Publication Data

US 2011/0021978 A1   Jan. 27, 2011

(51) Int. Cl.
*A61M 5/168*   (2006.01)
*A61M 5/172*   (2006.01)
(Continued)

(52) U.S. Cl.
CPC ......... *A61M 5/16827* (2013.01); *A61M 5/1408* (2013.01); *A61M 5/1723* (2013.01); *A61M 2005/1405* (2013.01); *A61M 2202/048* (2013.01); *A61M 2205/60* (2013.01); *A61M 2205/6036* (2013.01); *A61M 2205/6045* (2013.01); *A61M 2205/6072* (2013.01); *A61M 2230/30* (2013.01); *A61M 2230/42* (2013.01)

(58) Field of Classification Search
CPC ............. A61M 2205/6045; A61M 2205/6072; A61M 2205/6036; A61M 5/16827; A61M 5/1723; A61M 2205/3334; A61M 2230/42; A61M 2230/30; A61M 2205/60; A61M 2202/048; A61M 2202/041; A61M 2005/1405; A61M 5/140822
USPC .................. 604/65–67, 82, 512, 30
See application file for complete search history.

(56) References Cited

U.S. PATENT DOCUMENTS 5,293,913 A * 3/1994 Preszler ............... B41J 2/17523
141/100
5,530,531 A * 6/1996 Girard ........................... 399/120
(Continued)

FOREIGN PATENT DOCUMENTS

DE    102007010326    9/2008
JP    2001-509059 A   7/2001
(Continued)

OTHER PUBLICATIONS

PCT, International Search Report, International Application No. PCT/US2009/049934; 8 pages (Mar. 10, 2010).
(Continued)

*Primary Examiner* — Bhisma Mehta
*Assistant Examiner* — Jenna Zhang (57) ABSTRACT

A first drug delivery system includes first and second drug-container holders and first and second pump assemblies. The first (second) holder is adapted to receive a first (second) drug container having a first (a different second) dimensioned shape but not a second (first) drug container having a different second (a first) dimensioned shape. A second drug delivery system includes first and second bar code scanners, first and second drug-container holders, and first and second pump assemblies. The first (second) holder is adapted to receive a first (second) drug container having a dimensioned shape and to orient a positioned first (second) bar code of the first (second) drug container to face the first (second) bar code scanner because of the dimensioned shape. In one application, the first drug is a sedative drug, the second drug is an analgesic drug, and the drugs are used during a conscious sedation medical procedure.

10 Claims, 6 Drawing Sheets

(51) Int. Cl.
*A61M 5/142* (2006.01)
*A61M 5/14* (2006.01)

(56) References Cited

U.S. PATENT DOCUMENTS

| | | | |
|---|---|---|---|
| 5,807,316 | A | 9/1998 | Teeple, Jr. |
| 5,925,014 | A * | 7/1999 | Teeple, Jr. ............... A61J 3/002 128/203.13 |
| 6,043,273 | A * | 3/2000 | Duhaylongsod ....... A61K 31/00 514/478 |
| 6,071,933 | A | 6/2000 | Joo et al. |
| 6,929,041 | B2 * | 8/2005 | Falligant ............. A61M 16/183 141/351 |
| 7,229,430 | B2 | 6/2007 | Hickle et al. |
| 2002/0017299 | A1 | 2/2002 | Hickle |
| 2003/0040700 | A1 | 2/2003 | Hickle et al. |
| 2003/0074223 | A1 * | 4/2003 | Hickle et al. ..................... 705/2 |
| 2004/0073177 | A1 | 4/2004 | Hickle |
| 2004/0103897 | A1 | 6/2004 | Hickle et al. |
| 2005/0011916 | A1 * | 1/2005 | Battista ................ B41J 2/17509 222/576 |
| 2005/0177096 | A1 * | 8/2005 | Bollish ............. A61B 5/02055 604/65 |
| 2006/0009734 | A1 | 1/2006 | Martin |
| 2006/0042633 | A1 | 3/2006 | Bishop et al. |
| 2006/0100574 | A1 * | 5/2006 | Izumi ...................... A61J 3/002 604/82 |
| 2006/0206356 | A1 | 9/2006 | Vanderveen |
| 2007/0088271 | A1 * | 4/2007 | Richards ........... A61M 5/14244 604/151 |
| 2007/0191789 | A1 * | 8/2007 | Hickle .................. A61M 5/172 604/257 |
| 2007/0191817 | A1 | 8/2007 | Martin |
| 2007/0197978 | A1 * | 8/2007 | Wortham .......... A61M 5/14244 604/246 |
| 2007/0276270 | A1 | 11/2007 | Tran |
| 2008/0275425 | A1 | 11/2008 | Strickler et al. |
| 2009/0099552 | A1 | 4/2009 | Levy et al. |
| 2010/0010321 | A1 | 1/2010 | Foster |
| 2010/0010433 | A1 | 1/2010 | Krogh et al. |
| 2010/0038317 | A1 | 2/2010 | Bissler et al. |
| 2010/0137828 | A1 | 6/2010 | Michard et al. |
| 2010/0268065 | A1 | 10/2010 | Pile-Spellman et al. |

FOREIGN PATENT DOCUMENTS

| | | |
|---|---|---|
| JP | 2004-166847 A | 6/2004 |
| JP | 2004-194877 A | 7/2004 |
| JP | 2005-503202 A | 2/2005 |
| JP | 2005-509465 A | 4/2005 |
| JP | 2005-525885 A | 9/2005 |
| JP | 2006-511253 A | 4/2006 |
| JP | 2008-505692 | 2/2008 |
| JP | 2008-532635 A | 8/2008 |
| JP | 2009-082183 A | 4/2009 |
| WO | 2004/078033 | 9/2004 |
| WO | 2007/061368 | 5/2007 |

OTHER PUBLICATIONS

PCT, Invitation to Pay Additional Fees and Partial International Search Report, International Application No. PCT/US2010/041673 (Dec. 3, 2010).
PCT, International Search Report, International Application No. PCT/US2010/041673 (Feb. 16, 2011).
PCT, International Preliminary Report on Patentability, International Application No. PCT/US2010/041673 (Jan. 24, 2012).
EP, Communication (Comments on the Written Opinion and Amendment of the Application, European Application No. 10732823.9 (Feb. 28, 2012).
ECRI: "Patient-Controlled Analgesic Infusion Pump," *Health Devices*, vol. 35, No. 1, pp. 5-35 (Jan. 1, 2006).
ECRI: "General-Purpose Infusion Pumps," *Health Devices*, vol. 36, No. 10, pp. 309-336 (Oct. 1, 2007).
LeCouteur, C., "Intensive Care." *E. NZ Magazine*, Institute of Professional Engineers, New Zealand, vol. 6, No. 6, pp. 26-29 (Nov. 1, 2005).
JP, Notification of Reasons for Refusal, Japanese Application No. 2012-521671 (Jul. 1, 2014).
CN, Notification of First Office Action, Chinese Application No. 201080038338.6 (Mar. 28, 2013).
CN, Notification of Third Office Action, Chinese Application No. 201080038338.6 (Apr. 28, 2014).
JP, Notification of Reasons for Refusal, Japanese Application No. 2012-521671 (Mar. 11, 2014).

* cited by examiner

DRUG DELIVERY SYSTEM INCLUDING A DRUG-CONTAINER HOLDER AND A PUMP ASSEMBLY

FIELD OF THE INVENTION

The present invention is related generally to medical technology, and more particularly to a drug delivery system having a drug-container holder and a pump assembly.

BACKGROUND OF THE INVENTION

Known drug delivery systems include drug-delivery sedation systems such as drug-delivery conscious sedation systems. A known drug-delivery conscious sedation system is disclosed in United States Patent Application Publication No. 2002/0017299. In that system, a controller analyzed physiological parameters of the patient (such as blood pressure, etc.) and generated a request for a predetermined response from a patient. The controller analyzed the time delay between the request and the response to determine a level of sedation of the patient. When the time delay between the request and the response increased, the controller determined that the patient was in a deeper level of sedation and decreased the flow of a conscious sedation drug to the patient.

A drug delivery system is known wherein a drug vial containing a conscious sedation drug is placed on a spike of a drug-container holder of a drug-delivery cassette assembly to pierce the drug seal of the drug vial. A peristaltic pump is in fluid communication with a drug lumen of the spike, and a controller controls the pump to deliver the conscious sedation drug to the patient during a medical procedure. A pre-procedure bolus of an analgesic drug is also administered to the patient.

Still, scientists and engineers continue to seek improved drug delivery systems including a drug-container holder and a pump assembly.

SUMMARY OF THE INVENTION

A first expression of a first embodiment of the invention is for a drug delivery system including first and second drug-container holders and first and second pump assemblies. The first drug-container holder is adapted to receive a first drug container having a first dimensioned shape, wherein the first drug container contains a first drug, and wherein the first drug-container holder is adapted to access the first drug of the received first drug container. The second drug-container holder is adapted to receive a second drug container having a different second dimensioned shape, wherein the second drug container contains a different second drug, wherein the second drug-container holder is adapted to access the second drug of the received second drug container. The first drug-container holder is adapted to prevent receiving the second drug container because of the second dimensioned shape, and the second drug-container holder is adapted to prevent receiving the first drug container because of the first dimensioned shape. The first pump assembly is operatively connected to the first drug-container holder to access the first drug and is adapted to deliver the first drug to a patient. The second pump assembly is operatively connected to the second drug-container holder to access the second drug and is adapted to deliver the second drug to the patient. Of course other embodiments are possible in which two or more pump assemblies are used in conjunction with two or more drug-containers.

A second expression of a first embodiment of the invention is for a drug delivery system including first and second drug-container holders, first and second pump assemblies, and a controller. The first drug-container holder is adapted to receive a first drug container having a first dimensioned shape, wherein the first drug container contains a sedative drug, and wherein the first drug-container holder is adapted to access the sedative drug of the received first drug container. The second drug-container holder is adapted to receive a second drug container having a different second dimensioned shape, wherein the second drug container contains an analgesic drug, wherein the second drug-container holder is adapted to access the analgesic drug of the received second drug container. The first drug-container holder is adapted to prevent receiving the second drug container because of the second dimensioned shape, and the second drug-container holder is adapted to prevent receiving the first drug container because of the first dimensioned shape. The first pump assembly is operatively connected to the first drug-container holder to access the sedative drug and is adapted to deliver the sedative drug to a patient. The second pump assembly is operatively connected to the second drug-container holder to access the analgesic drug and is adapted to deliver the analgesic drug to the patient. The controller is operatively connected to the first and second pump assemblies. The controller is programmed to control a first flow rate of the first pump assembly to deliver the sedative drug to the patient during a medical procedure, and the controller is programmed to control a second flow rate of the second pump assembly to deliver the analgesic drug to the patient during the medical procedure.

A first expression of a second embodiment of the invention is for a drug delivery system including first and second bar code scanners, first and second drug-container holders, and first and second pump assemblies. The first drug-container holder is adapted to receive a first drug container having a first dimensioned shape and to orient a positioned first bar code of the first drug container to face the first bar code scanner because of the first dimensioned shape. The first drug container contains a first drug, and the first drug-container holder is adapted to access the first drug of the received first drug container. The second drug-container holder is adapted to receive a second drug container having a second dimensioned shape and to orient a positioned second bar code of the second drug container to face the second bar code scanner because of the second dimensioned shape. The second drug container contains a second drug, wherein the second drug-container holder is adapted to access the second drug of the received second drug container. The first pump assembly is operatively connected to the first drug-container holder to access the first drug and is adapted to deliver the first drug to a patient. The second pump assembly is operatively connected to the second drug-container holder to access the second drug and is adapted to deliver the second drug to the patient. In this embodiment, the first and second dimensioned shapes can be the same or they can be different. If they are the same, a shape is selected that forces the bar code to face the bar code scanner. The bar code scanner is the means to ensure correct drug and determine which pump is delivering the analgesic and which has the sedative.

A second expression of the second embodiment of the invention is for a drug delivery system including first and second bar code scanners, first and second drug-container holders, and first and second pump assemblies. The first drug-container holder is adapted to receive a first drug container having a first dimensioned shape and to orient a positioned first bar code of the first drug container to face the first bar code scanner because of the first dimensioned shape. In one aspect of this embodiment, the first drug container may contain a sedative drug, and the first drug-container holder is adapted to access the sedative drug of the received first drug container. The second drug-container holder is adapted to receive a second drug container having a second dimensioned shape and to orient a positioned second bar code of the second drug container to face the second bar code scanner because of the second dimensioned shape. In one aspect of this embodiment, the second drug container contains an analgesic drug, wherein the second drug-container holder is adapted to access the analgesic drug of the received second drug container. The first pump assembly is operatively connected to the first drug-container holder to access the sedative drug and is adapted to deliver the sedative drug to a patient. The second pump assembly is operatively connected to the second drug-container holder to access the analgesic drug and is adapted to deliver the analgesic drug to the patient. The controller is operatively connected to the first and second bar code scanners and to the first and second pump assemblies. The controller is programmed to verify for a medical procedure the identity of the sedative drug of the first drug container and the analgesic drug of the second drug container from the scanned first and second bar codes, and wherein, if verified, the controller is adapted to control a first flow rate of the first pump assembly to deliver the sedative drug to the patient during the medical procedure and to control a second flow rate of the second pump assembly to deliver the analgesic drug to the patient during the medical procedure. In another aspect of this embodiment, the first drug container may include the analgesic and the second drug container may include the sedative. Again, in this embodiment, the first and second dimensioned shapes can be the same or they can be different. If they are the same, a shape is selected that forces the bar code to face the bar code scanner. The bar code scanner is the means to ensure correct drug and determine which pump is delivering the analgesic and which has the sedative.

In a further aspect of the second embodiment, a loading dose of an analgesic (e.g., Fentanyl) may be delivered at the beginning of the procedure and then supplemental low volume doses delivered over a longer period of time (e.g., 1 mcg over 30 seconds). This delivery could be automated or delivered by a user action similar to a PRN. When Fentanyl is delivered, the system can take certain safety precautions to increase patient safety, such as prohibiting drug increase ("grey out up arrow"), reducing propofol delivery, ARM every 15 seconds, triggering reduced propofol or fentanyl at conservative levels (higher than yellow), triggering off of reduced respiratory rate, increased oxygen delivery, etc. These conservative actions could be limited to time intervals associated with the additional analgesic such as fentanyl.

Several benefits and advantages are obtained from one or more of the expressions of the embodiments of the invention. In one example of the first embodiment, the different dimensioned shapes prevent a user from installing the wrong drug container on a drug-container holder for a medical procedure which requires a controller to control the first pump assembly to deliver a sedative drug to a patient during a medical procedure and to control the second pump assembly to deliver an analgesic drug to the patient during the medical procedure. In one example of the second embodiment, the bar code scanners are used to prevent a user from using the wrong drug container on a drug-container holder for a medical procedure which requires a controller to control the first pump assembly to deliver a sedative drug to a patient during a medical procedure and to control the second pump assembly to deliver an analgesic drug to the patient during the medical procedure. In one illustration of either or both embodiments, a longer medical procedure can be performed which requires adjusting the flow rate of a sedative drug throughout a medical procedure and which requires adjusting the flow rate of an analgesic drug throughout the medical procedure, wherein the effects of a pre-treatment bolus of an analgesic drug would wear off before completion of the longer medical procedure.

DETAILED DESCRIPTION OF THE INVENTION

Before explaining several expressions of several embodiments of the invention in detail, it should be noted that each is not limited in its application or use to the details of construction and arrangement of parts, instructions, and steps illustrated in the accompanying drawings and description. The illustrative embodiments of the invention may be implemented or incorporated in other embodiments, variations, and modifications, and may be practiced or carried out in various ways. Furthermore, unless otherwise indicated, the terminology employed herein has been chosen for the purpose of describing the illustrative expressions of the embodiments of the present invention for the convenience of the reader and are not for the purpose of limiting the invention.

It is further understood that any one or more of the following-described expressions of a drug delivery system, implementations, etc. can be combined with any one or more of the other following-described expressions of a drug delivery system, implementations, etc.

A first embodiment of the invention is shown in FIGS. 1-5. A first expression of the embodiment of FIGS. 1-5 is for a drug delivery system 10 including first and second drug-container holders 12 and 14 and first and second pump assemblies 16 and 18. The first drug-container holder 12 is adapted to receive a first drug container 20 having a first dimensioned shape, wherein the first drug container 20 contains a first drug 22, and wherein the first drug-container holder 12 is adapted to access the first drug 22 of the received first drug container 20. The second drug-container holder 14 is adapted to receive a second drug container 24 having a different second dimensioned shape, wherein the second drug container 24 contains a different second drug 26, wherein the second drug-container holder 14 is adapted to access the second drug 26 of the received second drug container 24. The first drug-container holder 12 is adapted to prevent receiving the second drug container 24 because of the second dimensioned shape, and the second drug-container holder 14 is adapted to prevent receiving the first drug container 20 because of the first dimensioned shape. The first pump assembly 16 is operatively connected to the first drug-container holder 12 to access the first drug 22 and is adapted to deliver the first drug 22 to a patient 28. The second pump assembly 18 is operatively connected to the second drug-container holder 14 to access the second drug 26 and is adapted to deliver the second drug 26 to the patient 28.

Figure 1:
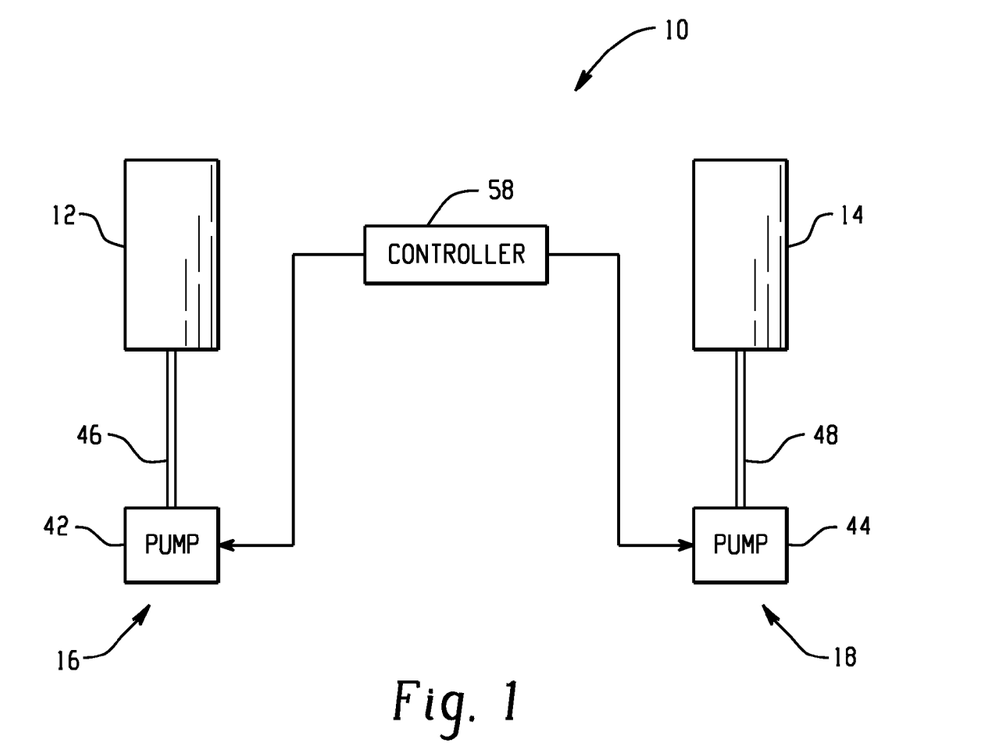
FIG. 1 is schematic diagram of a first embodiment of a drug delivery system of the invention including the first and second drug-container holders.
Figure 2:
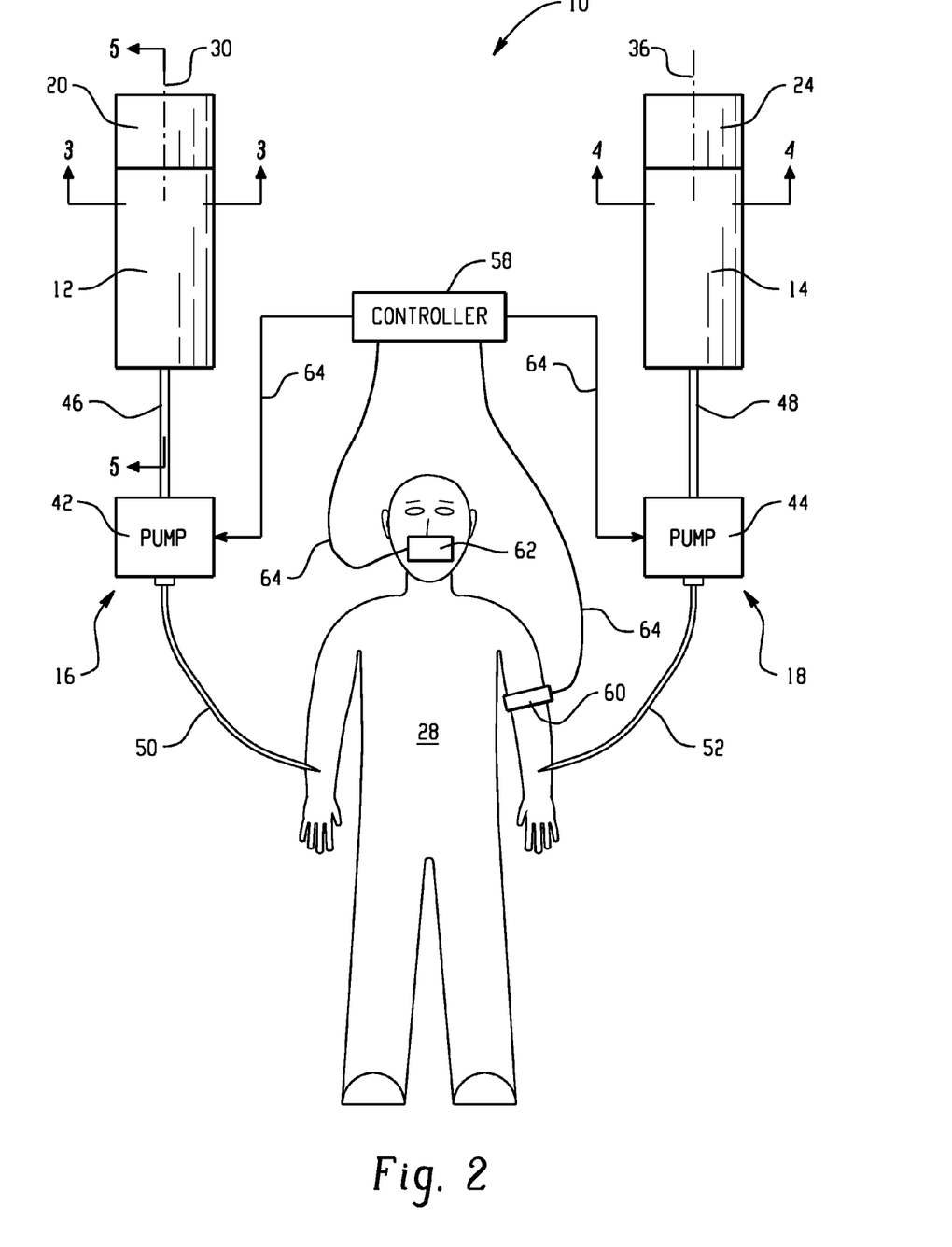
FIG. 2 is a view, as in FIG. 1, but with first and second drug containers installed, respectively, on the first and second drug-container holders and with the drug delivery system operatively connected to a patient.
Figure 3:
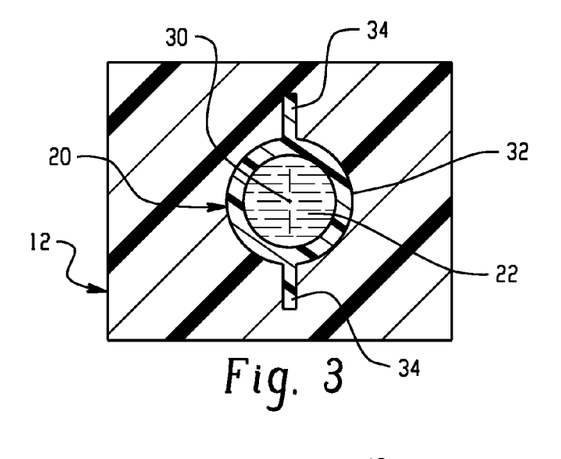
FIG. 3 is a cross-sectional view of the first drug-container holder and the first drug container of FIG. 2 taken along lines 3-3 of FIG. 2 showing the first dimensioned shape of the first drug container received by the first drug-container holder. While cylindrical containers are illustrated, any shape such as triangular, rectangular, hexagonal or polygonal could be used.

In one implementation of the first expression of the embodiment of FIGS. 1-5, the first drug container 20 has a first central longitudinal axis 30 (seen as a dashed line in FIG. 2 and as a dot in FIG. 3) and a coaxially-aligned first perimeter surface portion 32, wherein the first dimensioned shape at least includes the first perimeter surface portion 32. In one example, as seen in FIG. 3, the first perimeter surface portion 32 is a circle having two diametrically-opposed short or long ribs 34. In this example, the first drug-container holder 12 has an inner surface adapted to receive the first drug container 20, wherein the inner surface has a shape of a circle with two corresponding, diametrically-opposed, and longitudinally-extending inner-surface grooves. In this example, the first drug container 20 has a first plug shape, and the first drug-container holder 12 has a corresponding first receptacle shape to engagingly receive the first drug container 20 (but not the second drug container 24).

In the same or a different implementation, the second drug container 24 has a second central longitudinal axis 36 and a coaxially-aligned second perimeter surface portion 38, wherein the second dimensioned shape at least includes the second perimeter surface portion 38. In one example, seen in FIG. 4, the second perimeter surface portion 38 is a circle having three ribs 40 located, respectively, at 0 degrees (the top rib 40), at 135 degrees (the lower right rib 40), and at 225 degrees (the lower left rib 40). In this example, the second drug-container holder 14 has an inner surface adapted to receive the second drug container 24, wherein the inner surface has a shape of a circle with three corresponding and longitudinally-extending inner-surface grooves located, respectively, at 0 degrees, 135 degrees, and 225 degrees. In this example, the second drug container 24 has a second plug shape, and the second drug-container holder 14 has a corresponding second receptacle shape to engagingly receive the second drug container 24 (but not the first drug container 20).

Figure 4:
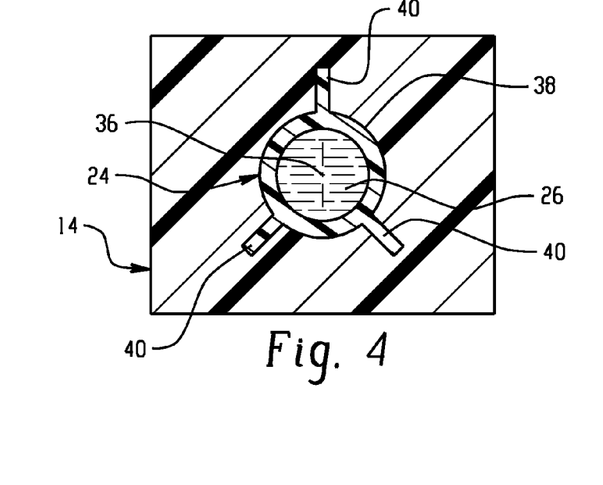
FIG. 4 is a cross-sectional view of the second drug-container holder and the second drug container of FIG. 2 taken along lines 4-4 of FIG. 2 showing the second dimensioned shape of the second drug container received by the second drug-container holder.
Figure 5:
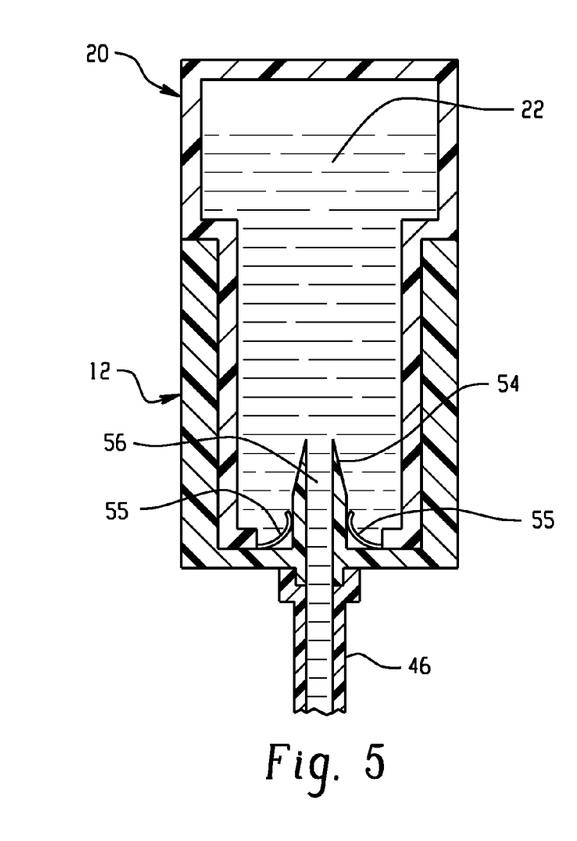
FIG. 5 is a cross-sectional view of the first drug-container holder and the first drug container of FIG. 2 taken along lines 5-5 of FIG. 2 showing the spike of the first drug-container holder having pierced the drug seal of the first drug container.
Figure 6:
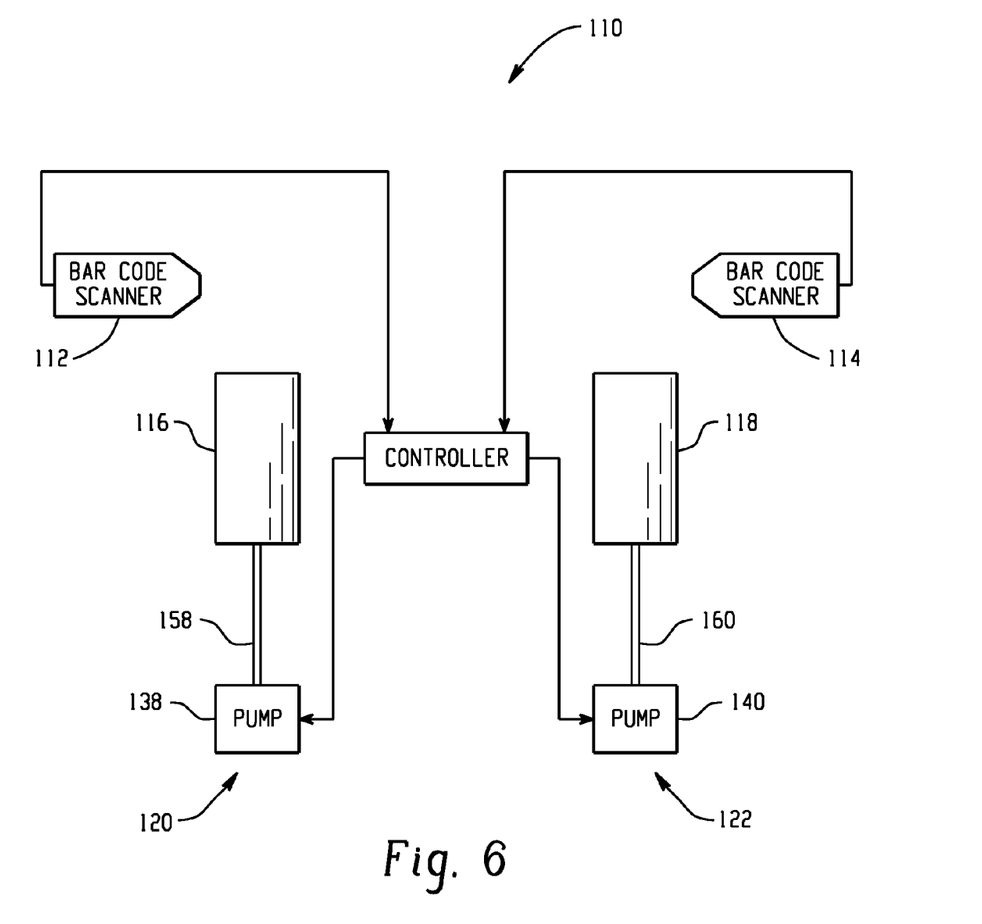
FIG. 6 is a schematic view of a second embodiment of a drug delivery system of the invention including the first and second drug-container holders and the first and second bar code scanners.
Figure 7:
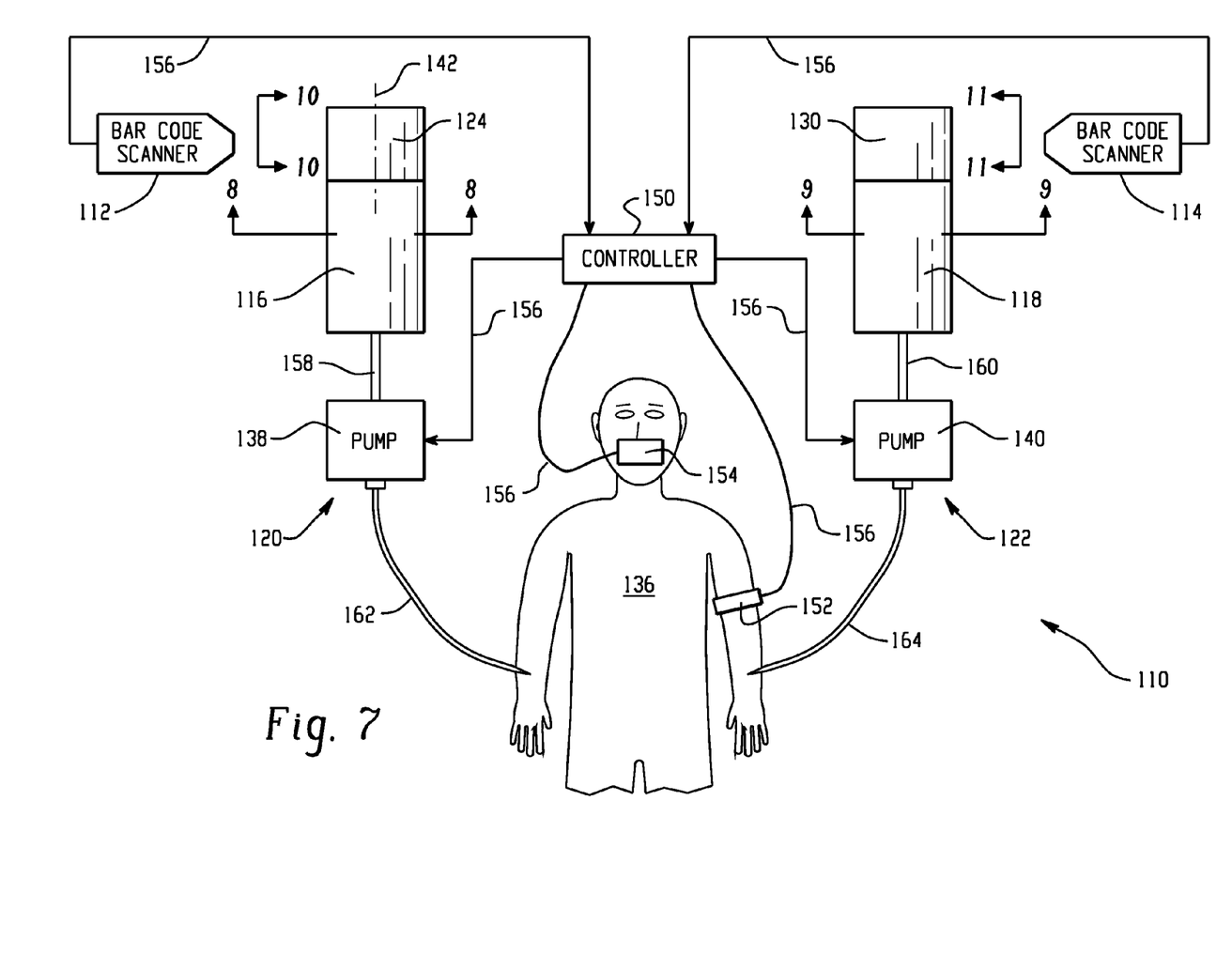
FIG. 7 is a view, as in FIG. 6, but with first and second drug containers installed, respectively, on the first and second drug-container holders and with the drug delivery system operatively connected to a patient.
Figure 8:
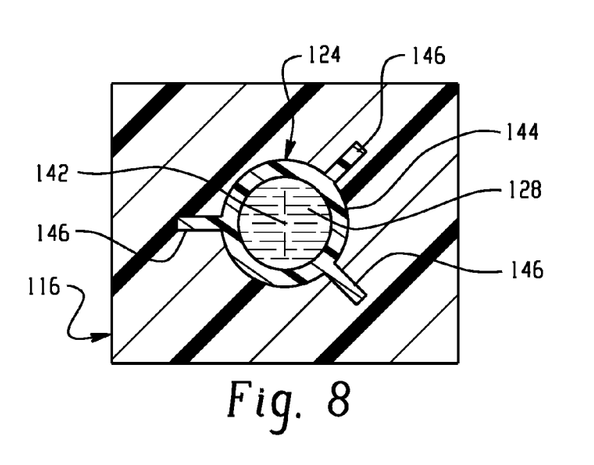
FIG. 8 is a cross-sectional view of the first drug-container holder and the first drug container of FIG. 7 taken along lines 8-8 of FIG. 7 showing the first dimensioned shape of the first drug container received by the first drug-container holder.
Figure 9:
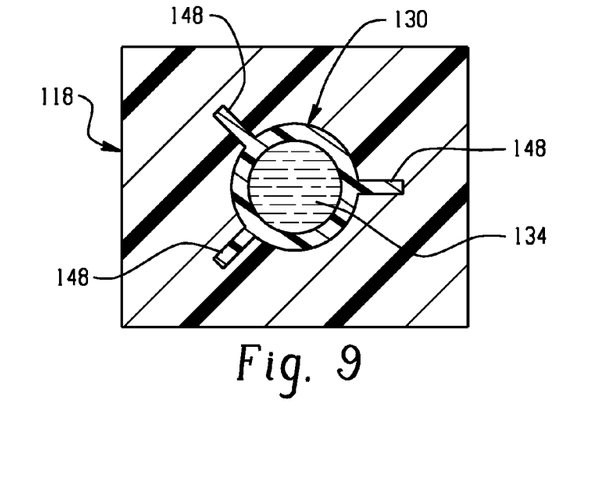
FIG. 9 is a cross-sectional view of the second drug-container holder and the second drug container of FIG. 7 taken along lines 9-9 of FIG. 7 showing the second dimensioned shape of the second drug container received by the second drug-container holder to be the same as the first dimensioned shape.

It is noted that the first dimensioned shape of the first drug container 20 seen in FIG. 3 prevents it from being received by the second drug-container holder 14 seen in FIG. 4, and the second dimensioned shape of the second drug container 24 seen in FIG. 4 prevents it from being received by the first drug-container holder 12 seen in FIG. 3. Other first and second dimensioned shapes are left to those skilled in the art (e.g., angular, polygonal, arcuate, ribbed etc.). It is also noted that a small circle and a large circle may be said to have the same shape, but they do not have the same dimensioned shape because the small circle is of small dimension and the large circle is of large dimension.

In one enablement of the first expression of the embodiment of FIGS. 1-5, the first drug 22 is a sedative drug, the second drug 26 is an analgesic drug, and the medical procedure is a conscious sedation (a/k/a minimal-to-moderate sedation) medical procedure. In a first different enablement, both drugs are different sedative or different analgesic drugs. In a second different enablement, one of the two drugs is a sedative or analgesic drug, and the other of the two drugs is an amnesic drug. Other different drugs for other enablements are left to the artisan.

In one application of the first expression of the embodiment of FIGS. 1-5, the first and second drug containers 20 and 24 are, respectively, first and second drug vials. Other types of drug containers include, without variation, pre-filled drug syringes. In the same or a different application, the first and second pump assemblies 16 and 18 each include an intravenous infusion pump 42 and 44. In one example, the intravenous infusion pumps 42 and 44 each are intravenous-infusion peristaltic pumps. Other types of pump assemblies are left to the artisan.

In one construction of the first expression of the embodiment of FIGS. 1-5, tubing 46 and 48 carries, respectively, the first drug 22 from the first drug-container holder 12 to the first pump assembly 16 and the second drug 26 from the second drug-container holder 14 to the second pump assembly 18. In the same or different construction, intravenous tubes 50 and 52 carry, respectively, the first drug 22 from the first pump assembly 16 to the patient 28 and the second drug 26 from the second pump assembly 18 to the patient 28.

In one arrangement of the first expression of the embodiment of FIGS. 1-5, the first drug-container holder 12 includes a spike 54 which pierces the drug seal 55 of the first drug container 20 when the first drug container 20 is received by the first drug-container holder 12. The spike 54 includes a drug lumen 56 to carry the first drug 22 from the first drug container 20 to the tubing 46. It is noted that an air-supply lumen of the spike 54 has been omitted from FIG. 5 for clarity.

A second expression of the embodiment of FIGS. 1-5 is identical to the first expression of paragraph [0028] with the first drug 22 being a sedative drug, with the second drug 26 being an analgesic drug, and with the addition of a controller 58. The controller 58 is operatively connected to the first and second pump assemblies 16 and 18. The controller 58 is programmed to control a first flow rate of the first pump assembly 16 to deliver the sedative drug (when the first drug 22 is a sedative drug) to the patient 28 during a medical procedure, and the controller 58 is programmed to control a second flow rate of the second pump assembly 18 to deliver the analgesic drug (when the second drug 26 is an analgesic drug) to the patient 28 during the medical procedure.

It is noted that the implementations, applications, arrangements, etc. of the first expression of the embodiment of FIGS.

1-5 are equally applicable to the second expression of the embodiment of FIGS. 1-5. While the invention is illustrated using a system employing two containers, it will be apparent that any suitable number of containers could be accommodated by the teachings herein.

In one extension of the second expression of the embodiment of FIGS. 1-5, The controller 58 is programmed to receive a plurality of physiological parameters of the patient 28 during the medical procedure, and the controller 58 is programmed to adjust at least one of the first and second flow rates as a function of at least the received physiological parameters. In one example, the physiological parameters include blood pressure and respiratory rate, wherein the blood pressure is derived using an automated blood pressure cuff 60 operatively connected to the patient 28, and the respiratory rate is derived using pressure measurements from an oral-nasal cannula 62 operatively connected to the patient 28, such blood pressure and respiratory rate derivations being well known to those skilled in the art. In one illustration, cables 64 separately connect the controller 58 to the first and second pump assemblies 16 and 18 and separately connect the controller 58 to the blood pressure cuff 60 and the oral-nasal cannula 62. Other operative connections include, without limitation, wireless communications.

In one realization of the first and/or second expression of the embodiment of FIGS. 1-5, the drug delivery system 10 includes the first and second drug containers 20 and 24.

A second embodiment of the invention is shown in FIGS. 6-11. A first expression of the embodiment of FIGS. 6-11 is for a drug delivery system 110 including first and second bar code scanners 112 and 114, first and second drug-container holders 116 and 118, and first and second pump assemblies 120 and 122. The first drug-container holder 116 is adapted to receive a first drug container 124 having a first dimensioned shape and to orient a positioned first bar code 126 of the first drug container 124 to face the first bar code scanner 112 because of the first dimensioned shape. The first drug container 124 contains a first drug 128, and the first drug-container holder 116 is adapted to access the first drug 128 of the received first drug container 124. The second drug-container holder 118 is adapted to receive a second drug container 130 having a second dimensioned shape and to orient a positioned second bar code 132 of the second drug container 130 to face the second bar code scanner 114 because of the second dimensioned shape. The second drug container 130 contains a second drug 134, wherein the second drug-container holder 118 is adapted to access the second drug 134 of the received second drug container 130. The first pump assembly 120 is operatively connected to the first drug-container holder 116 to access the first drug 128 and is adapted to deliver the first drug 128 to a patient 136. The second pump assembly 122 is operatively connected to the second drug-container holder 118 to access the second drug 134 and is adapted to deliver the second drug 134 to the patient 136.

In one enablement of the first expression of the embodiment of FIGS. 6-11, the first drug 128 is a sedative drug, the second drug 134 is an analgesic drug, and the medical procedure is a conscious sedation medical procedure. In one application of the first expression of the embodiment of FIGS. 6-11 the first and second drug containers 124 and 130 are, respectively, first and second drug vials. In the same or a different application, the first and second pump assemblies 120 and 122 each include an intravenous infusion pump 138 and 140.

In one arrangement of the first expression of the embodiment of FIGS. 6-11, the first and second dimensioned shapes are the same (although in a different arrangement, not shown, they are different). In one implementation, the first drug container 124 has a first central longitudinal axis 142 and a coaxially-aligned first perimeter surface portion 144, wherein the first dimensioned shape at least includes the first perimeter surface portion 144. In one example, seen in FIG. 8, the first perimeter surface portion 144 is a circle having three ribs 146 located, respectively, at 45 degrees (the upper right rib 146), at 135 degrees (the lower right rib 146), and at 270 degrees (the left rib 146). Other shapes may also be used.

Figure 10:
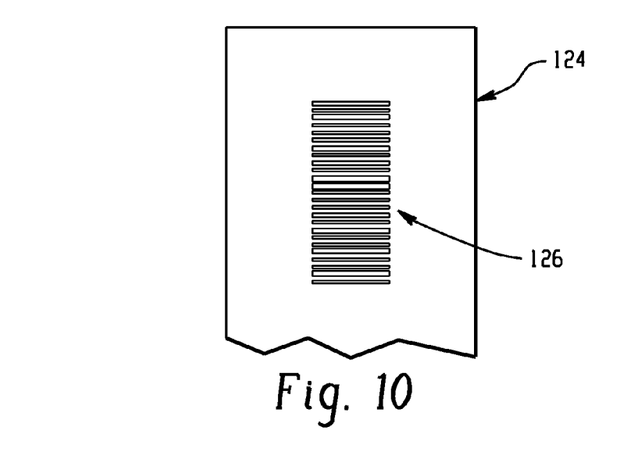
FIG. 10 is a view of the bar code region of the first drug container of FIG. 7 taken along lines 10-10 of FIG. 7.

In this example, the first drug-container holder 116 has an inner surface adapted to receive the first drug container 124, wherein the inner surface has a shape of a circle with three corresponding and longitudinally-extending inner-surface grooves located, respectively, at 45 degrees, 135 degrees, and 270 degrees. In this example, the first drug container 124 has a first plug shape, and the first drug-container holder 116 has a corresponding first receptacle shape to engagingly receive the first drug container 124. In this example, as seen in FIG. 10, the first bar code 126 is positioned on the first drug container 124 in FIG. 7 to be rotationally aligned with the left rib 146 in FIG. 8 so that the first bar code 126 of the received first drug container 124 can be scanned by the first bar code scanner 112.

Figure 11:
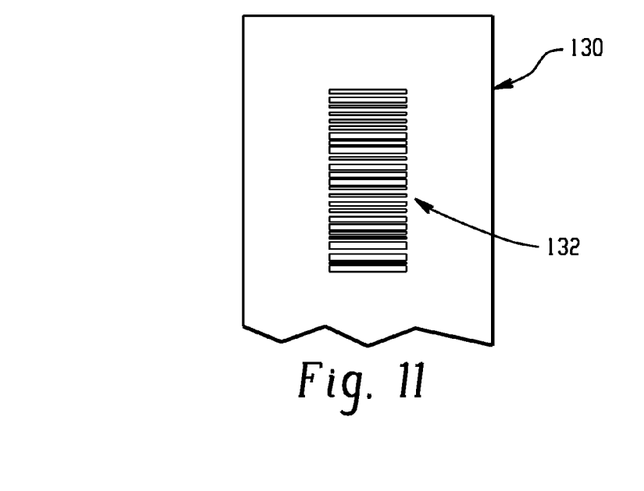
FIG. 11 is a view of the bar code region of the second drug container of FIG. 7 taken along lines 11-11 of FIG. 7.

In this example, the second dimensioned shape (seen in FIG. 9) is the same as the first dimensioned shape (seen in FIG. 8) but rotated 180 degrees. In this example, as seen in FIG. 11, the second bar code 132 is positioned on the second drug container 130 in FIG. 7 to be rotationally aligned with the right rib 148 of the second drug container 130 in FIG. 9 so that the second bar code 132 of the received second drug container 130 can be scanned by the second bar code scanner 114.

A second expression of the embodiment of FIGS. 6-11 is identical to the first expression of paragraph [0040] with the first drug 128 being a sedative drug, with the second drug 134 being an analgesic drug, and with the addition of a controller 150. The controller 150 is operatively connected to the first and second bar code scanners 112 and 114 and to the first and second pump assemblies 120 and 122. The controller 150 is programmed to verify for a medical procedure the identity of the sedative drug of the first drug container 124 and the analgesic drug of the second drug container 130 from the scanned first and second bar codes 126 and 132, and wherein, if verified, the controller 150 is adapted to control a first flow rate of the first pump assembly 120 to deliver the sedative drug to the patient 136 during the medical procedure and to control a second flow rate of the second pump assembly 122 to deliver the analgesic drug to the patient 136 during the medical procedure.

It is noted that the implementations, applications, arrangements, etc. of the first expression of the embodiment of FIGS. 1-5 are equally applicable to the second expression of the embodiment of FIGS. 6-11. It is noted, as in the embodiment of FIG. 2, the embodiment of FIG. 7 also shows a blood pressure cuff 152, an oral-nasal cannula 154, cables 156, tubing 158 and 160, and intravenous tubes 162 and 164.

In one extension of the second expression of the embodiment of FIGS. 6-11, the controller 150 is programmed to receive a plurality of physiological parameters of the patient 136 during the medical procedure, and the controller 150 is programmed to adjust at least one of the first and second flow rates as a function of at least the received physiological parameters. In one example, the physiological parameters include blood pressure and respiratory rate, wherein the blood pressure is derived using an automated blood pressure cuff 152 operatively connected to the patient 136, and the respiratory rate is derived using pressure measurements from an oral-nasal cannula 154 operatively connected to the patient 136, such blood pressure and respiratory rate derivations being well known to those skilled in the art. In one illustration, cables 156 separately connect the controller 150 to the first and second bar code scanners 112 and 114, separately connect the controller 150 to the first and second pump assemblies 120 and 122, and separately connect the controller 150 to the blood pressure cuff 152 and the oral-nasal cannula 154. Other operative connections include, without limitation, wireless communications.

In one realization of the first and/or second expression of the embodiment of FIGS. 6-11, the drug delivery system 110 includes the first and second drug containers 124 and 130.

Several benefits and advantages are obtained from one or more of the expressions of the embodiments of the invention. In one example of the first embodiment, the different dimensioned shapes prevent a user from installing the wrong drug container on a drug-container holder for a medical procedure which requires a controller to control the first pump assembly to deliver a sedative drug to a patient during a medical procedure and to control the second pump assembly to deliver an analgesic drug to the patient during the medical procedure. In one example of the second embodiment, the bar code scanners are used to prevent a user from using the wrong drug container on a drug-container holder for a medical procedure which requires a controller to control the first pump assembly to deliver a sedative drug to a patient during a medical procedure and to control the second pump assembly to deliver an analgesic drug to the patient during the medical procedure. In one illustration of either or both embodiments, a longer medical procedure can be performed which requires adjusting the flow rate of a sedative drug throughout a medical procedure and which requires adjusting the flow rate of an analgesic drug throughout the medical procedure, wherein the effects of a pre-treatment bolus of an analgesic drug would wear off before completion of the longer medical procedure.

While the present invention has been illustrated by several expressions of several embodiments, and enablements, applications, etc. thereof, it is not the intention of the applicant to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended Claims.

What is claimed is:

1. A drug delivery system comprising:
a) a first bar code scanner;
b) a first drug-container holder adapted to receive a first drug container having a first dimensioned shape and to orient a positioned first bar code of the first drug container to face the first bar code scanner because of the first dimensioned shape, wherein the first drug container contains a first drug, and wherein the first drug-container holder is adapted to access the first drug of the received first drug container;
c) a second bar code scanner;
d) a second drug-container holder adapted to receive a second drug container having a second dimensioned shape and to orient a positioned second bar code of the second drug container to face the second bar code scanner because of the second dimensioned shape that may be the same or different than the first dimensioned shape, wherein the second drug container contains a second drug, wherein the second drug-container holder is adapted to access the second drug of the received second drug container;
e) a first pump assembly operatively connected to the first drug-container holder to access the first drug and adapted to deliver the first drug to a patient; and
f) a second pump assembly operatively connected to the second drug-container holder to access the second drug and adapted to deliver the second drug to the patient,
wherein the first drug container has a first central longitudinal axis and a rotationally-asymmetric, coaxially-aligned first perimeter surface portion, wherein the first dimensioned shape at least includes the first perimeter surface portion, and wherein the first drug container holder includes a rotationally-asymmetric first inner surface portion conformingly corresponding in shape to the first perimeter surface portion of the first dimensioned shape, the rotationally-asymmetric first inner surface portion linearly receiving the rotationally-asymmetric, coaxially-aligned first perimeter surface portion over final insertion of the first drug container into the first drug-container holder.

2. The drug delivery system of claim 1, wherein the first drug is a sedative drug and the second drug is an analgesic drug.

3. The drug delivery system of claim 2 wherein the system is adapted to automatically deliver a loading dose of the analgesic drug to the patient at the start of the medical procedure, and subsequently at least one supplemental low volume dose of the analgesic drug over a prolonged period of time.

4. The drug delivery system of claim 1, wherein the first and second drug containers are, respectively, first and second drug vials, and wherein the first and second pump assemblies each include an intravenous infusion pump configured to separately deliver the respective drugs to the patient.

5. The drug delivery system of claim 1, wherein the first and second shapes are the same.

6. A drug delivery system comprising:
a) a first bar code scanner;
b) a first drug-container holder adapted to receive a first drug container having a first dimensioned shape and to orient a positioned first bar code of the first drug container to face the first bar code scanner because of the first dimensioned shape, wherein the first drug container contains a sedative drug, and wherein the first drug-container holder is adapted to access the sedative drug of the received first drug container;
c) a second bar code scanner;
d) a second drug-container holder adapted to receive a second drug container having a second dimensioned shape that is the same or different than the first dimensioned shape and to orient a positioned second bar code of the second drug container to face the second bar code scanner because of the second dimensioned shape, wherein the second drug container contains an analgesic drug, wherein the second drug-container holder is adapted to access the analgesic drug of the received second drug container;
e) a first pump assembly operatively connected to the first drug-container holder to access the sedative drug and adapted to deliver the sedative drug to a patient;
f) a second pump assembly operatively connected to the second drug-container holder to access the analgesic drug and adapted to deliver the analgesic drug to the patient; and g) a controller operatively connected to the first and second bar code scanners and to the first and second pump assemblies, wherein the controller is programmed to verify for a medical procedure the identity of the sedative drug of the first drug container and the analgesic drug of the second drug container from the scanned first and second bar codes, and wherein, if verified, the controller is adapted to control a first flow rate of the first pump assembly to deliver the sedative drug to the patient during the medical procedure and to control a second flow rate of the second pump assembly to deliver the analgesic drug to the patient during the medical procedure, wherein the first drug container has a first central longitudinal axis and a rotationally-asymmetric, coaxially-aligned first perimeter surface portion, wherein the first dimensioned shape at least includes the rotationally-asymmetric, coaxially-aligned first perimeter surface portion, and wherein the first drug container holder includes a rotationally-asymmetric first inner surface portion conformingly corresponding in shape to the rotationally-asymmetric, coaxially-aligned first perimeter surface portion of the first dimensioned shape, with the rotationally-asymmetric first inner surface portion linearly receiving the rotationally-asymmetric, coaxially-aligned first perimeter surface portion over final insertion of the first drug container into the first drug-container holder.

7. The drug delivery system of claim 6, wherein the first and second drug containers are, respectively, first and second drug vials, and wherein the first and second pump assemblies each include an intravenous infusion pump configured to separately deliver the respective drugs to the patient.

8. The drug delivery system of claim 6, wherein the first and second dimensioned shapes are the same.

9. The drug delivery system of claim 6, wherein the controller is programmed to receive a plurality of physiological parameters of the patient during delivery of the sedative and analgesic drugs to the patient, and wherein the controller is programmed to adjust at least one of the first and second flow rates as a function of at least the received physiological parameters.

10. The drug delivery system of claim 6 wherein the controller is programmed to deliver a loading dose of the analgesic drug to the patient at the start of the medical procedure, and subsequently at least one supplemental low volume dose of the analgesic drug is delivered over a prolonged period of time.

* * * * *